United States Patent
Lorenzo

(10) Patent No.: US 9,993,624 B2
(45) Date of Patent: Jun. 12, 2018

(54) STEP FEATURE FOR STEERABLE GUIDEWIRES

(71) Applicant: DePuy Synthes Products, INC., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 284 days.

(21) Appl. No.: 14/454,780

(22) Filed: Aug. 8, 2014

(65) Prior Publication Data

US 2016/0038721 A1  Feb. 11, 2016

(51) Int. Cl.
*A61M 25/09* (2006.01)
*A61F 2/962* (2013.01)
(Continued)

(52) U.S. Cl.
CPC .............. *A61M 25/09* (2013.01); *A61F 2/962* (2013.01); *A61M 25/0133* (2013.01);
(Continued)

(58) Field of Classification Search
CPC ........ A61M 25/09; A61M 2025/09175; A61M 2025/09183; A61M 2025/09125; A61B 17/12118; A61B 2/954; A61B 2/962; A61B 2002/9534; A61F 2/954; A61F 2/962; A61F 2002/9534
(Continued)

(56) References Cited

U.S. PATENT DOCUMENTS 5,002,560 A * 3/1991 Machold ............... A61M 29/02
604/104
5,265,622 A  11/1993 Barbere
(Continued)

FOREIGN PATENT DOCUMENTS

WO  2006119503 A1  11/2006
WO  2007033052 A2  3/2007

OTHER PUBLICATIONS

Percent. (1992). In C. Morris (Ed.), Academic press Dictionary of science and technology. Oxford, United Kingdom: Elsevier Science & Technology. Retrieved from <http://search.credoreference.com/content/entry/apdst/percent/0> on Mar. 26, 2016.*
(Continued)

*Primary Examiner* — David J McCrosky
(74) *Attorney, Agent, or Firm* — Troutman Sanders LLP

(57) ABSTRACT

A mechanism can include a step feature guidewire having a guidewire with a proximal end, a distal end, and a diameter. A self-expanding element can be disposed approximate to the distal end of the guidewire and can have at least two states which include a contracted diameter and an expanded diameter. The self-expanding element can be expandable under its inherent properties, based at least on its original shape and the nature of the materials that make up the element. Further, the expanded diameter can be approximately 70% to 280% of the guidewire diameter. While the guidewire is designed for passing through a body lumen while treating a patient, the expanded diameter is less than any body lumen diameter the guidewire is determined to pass through.

12 Claims, 8 Drawing Sheets

(51) Int. Cl.
  *A61M 25/01* (2006.01)
  *A61M 25/10* (2013.01)
(52) U.S. Cl.
  CPC ............... *A61M 2025/0177* (2013.01); *A61M 2025/09125* (2013.01); *A61M 2025/09175* (2013.01); *A61M 2025/09183* (2013.01); *A61M 2025/1004* (2013.01)
(58) Field of Classification Search
  USPC ....................................................... 623/1.11
  See application file for complete search history.

(56) References Cited

U.S. PATENT DOCUMENTS

| | | | |
|---|---|---|---|
| 5,273,052 A | | 12/1993 | Kraus et al. |
| 5,447,503 A | | 9/1995 | Miller |
| 5,497,782 A | | 3/1996 | Fugoso |
| 6,843,798 B2 | * | 1/2005 | Kusleika ................... A61F 2/01 |
| | | | 606/200 |
| 6,932,829 B2 | | 8/2005 | Majercak |
| 8,142,468 B2 | | 3/2012 | Inderbitzen et al. |
| 2007/0021685 A1 | | 1/2007 | Oepen et al. |
| 2015/0289965 A1 | * | 10/2015 | Kusleika ................. A61F 2/013 |
| | | | 606/200 |

OTHER PUBLICATIONS

European Partial Search Report dated Jan. 4, 2016, issued in corresponding Application No. 15180176.8-1506.

* cited by examiner

PRIOR ART

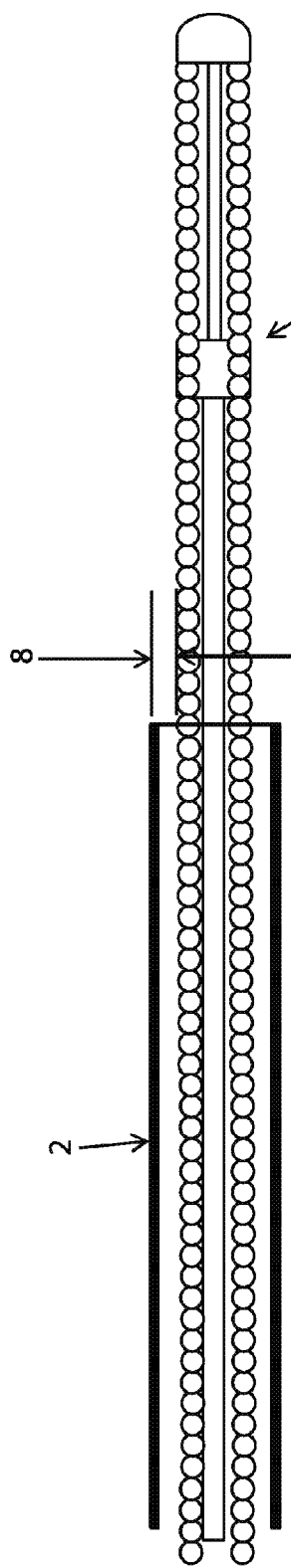
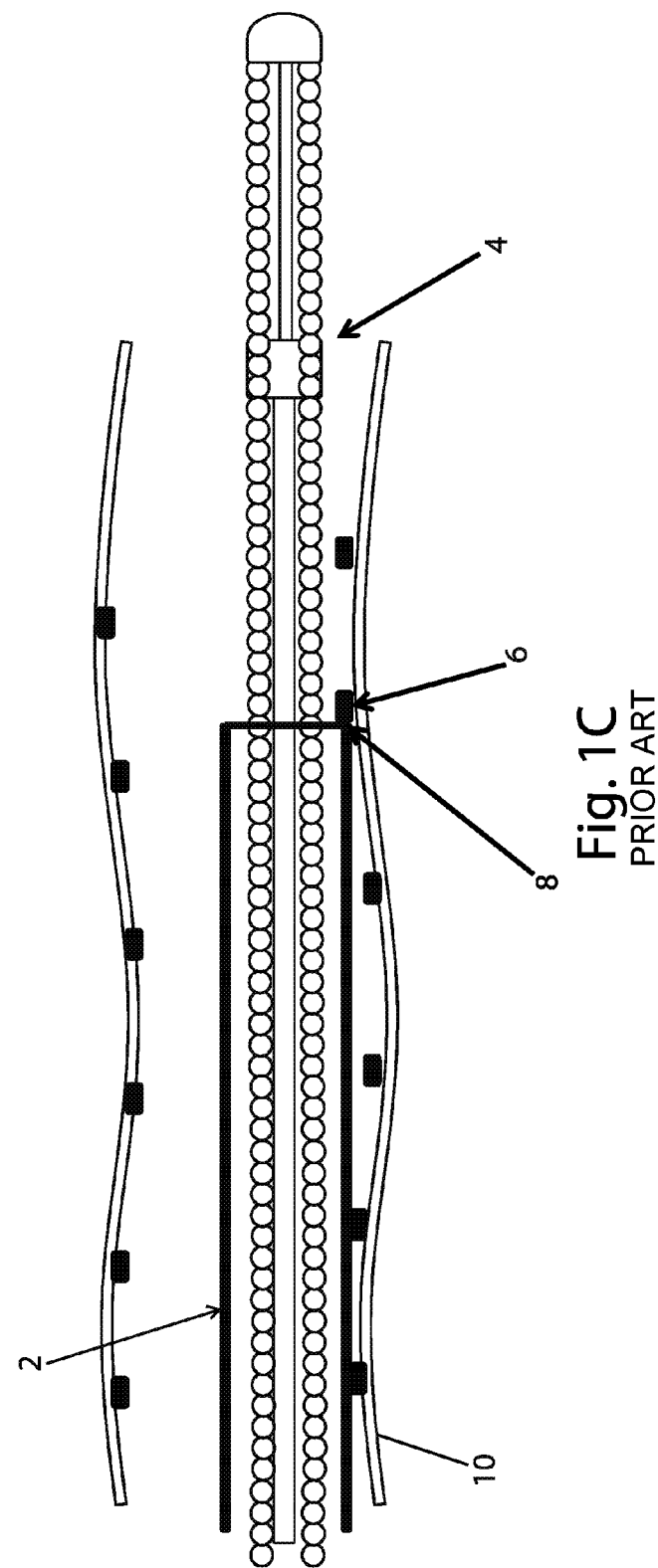
Fig. 1B
PRIOR ART
Fig. 1C
PRIOR ART

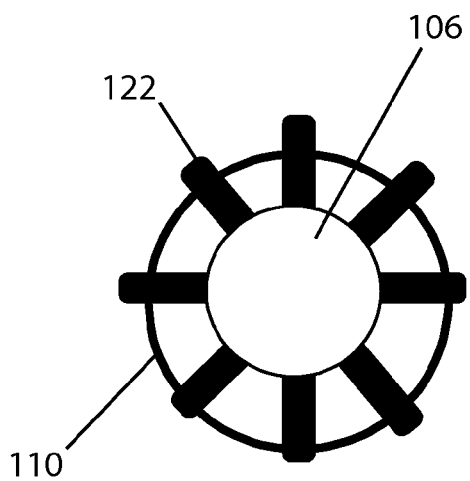
Fig. 3
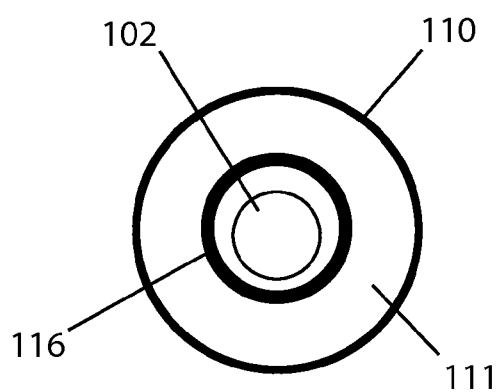
Fig. 4
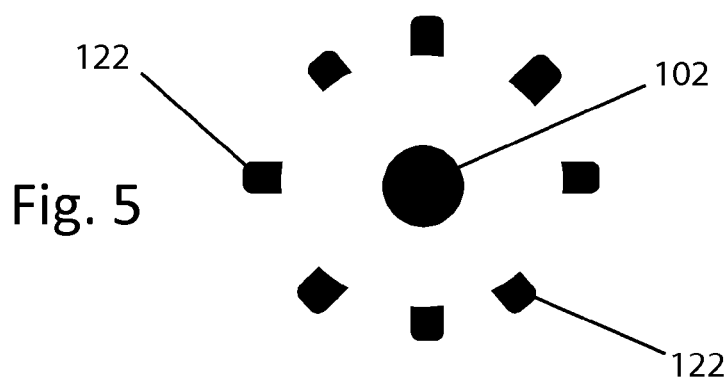
Fig. 5
Fig. 6
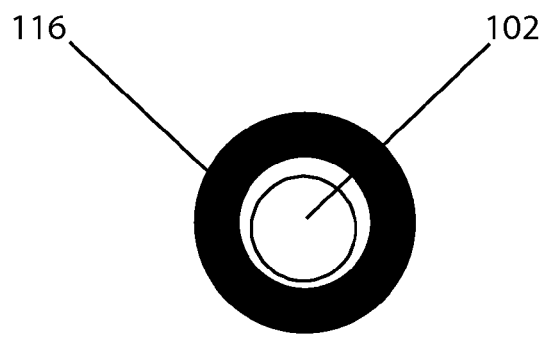

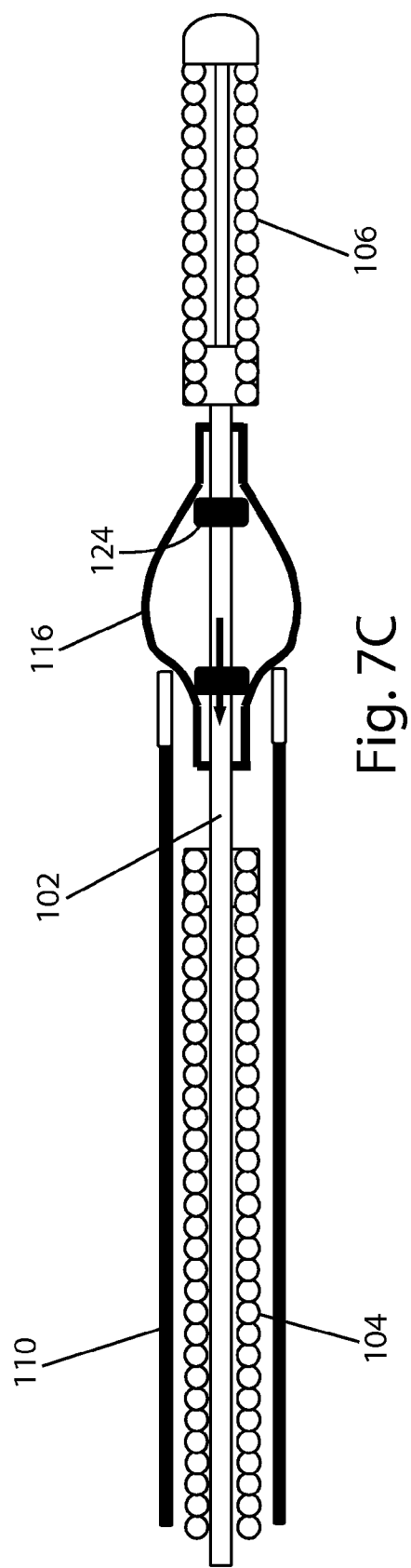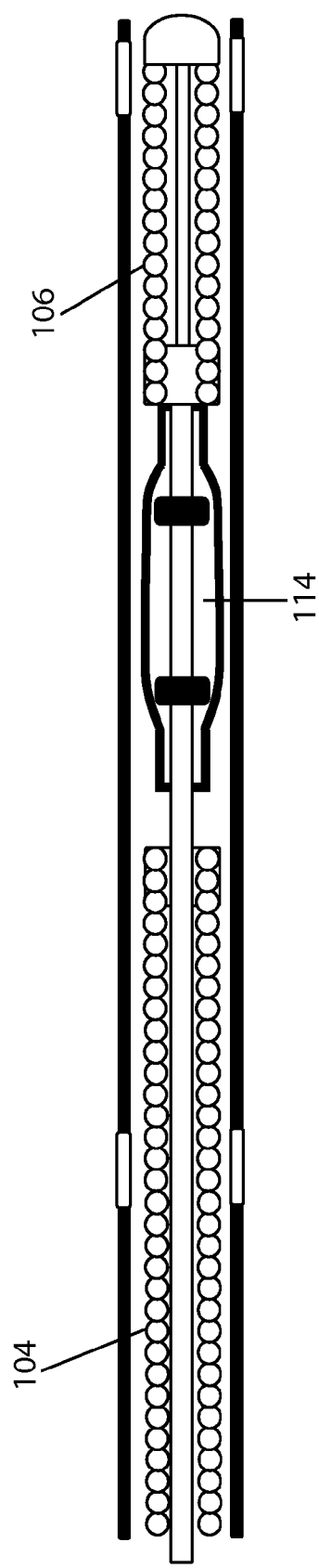
Fig. 7C
Fig. 7D

STEP FEATURE FOR STEERABLE GUIDEWIRES

FIELD OF THE INVENTION

This invention relates to a self-expanding feature that can be integrated into a distal aspect of a guidewire to facilitate the crossing of a previously deployed device in the vasculature with a catheter or microcatheter.

BACKGROUND

Crossing a previously deployed intravascular stent with a catheter over a guidewire presents a challenge, especially during neurovascular procedures. Often it is not possible to advance a catheter over the guidewire because of a ledge formed between the outer diameter of the guidewire and the outer diameter of the catheter. FIG. 1A illustrates a microcatheter 2 with a guidewire 4, therethrough, hung up on a stent strut 6. FIG. 1A is a forward view of the catheter 2 over the wire 4 crossing through the stent cell 10 and getting caught on the stent struts 6 (as in the case of an aneurysm coiling procedure) because of the difference in diameters of the guidewire 4 and the catheter 2. FIG. 1B illustrates the ledge 8, as the difference between the outer diameter of the guidewire 4 and the outer diameter of the microcatheter 2. The ledge 8 distance can actually be greater as the guidewire 4 can be displaced from a center axis of the microcatheter 2, creating even more of a gap. FIG. 1C illustrates the above problem. The stent cell 10 is placed within a body lumen (not illustrated) and the guidewire 4 is guided through the lumen. The microcatheter 2 is then advanced along the guidewire 4 and gets hung up on the stent strut 6 at the ledge 8.

Prior art attempts to solve this problem included "rounding" or "beveling" the tip of the catheter to facilitate tracking over the struts of the device. Additionally, a multi-catheter configuration has been tried in which catheters of progressively smaller diameters are inserted coaxially inside each other to minimize the ledge.

What is needed is a simple mechanism to prevent the ledge 8 from catching on the stent strut 6 while still being able to advance the guidewire 4 and microcatheter 2.

SUMMARY

A mechanism to help prevent the ledge of the prior art can include a step feature guidewire having a guidewire with a proximal end, a distal end, and a diameter. A self-expanding element can be disposed approximate to the distal end of the guidewire and can have at least two states which include a contracted diameter and an expanded diameter. The self-expanding element can be expandable under its inherent properties, based at least on its original shape and the nature of the materials that make up the element. Further, the expanded diameter can be approximately 70% to 280% of the guidewire diameter. While the guidewire is designed for passing through a body lumen while treating a patient, the expanded diameter is less than any body lumen diameter the guidewire is determined to pass through.

Examples of the self-expanding element can be one of pear shaped, ovoid, and elliptical when at its expanded diameter. These can act as a "ramp" to get the catheter over any obstacle in the body lumen, e.g. a previously implanted stent. Also, the self-expanding element can include a plurality of deformable leafs. In another example of a step feature guidewire, a bump can be disposed on the guidewire under the self-expanding element and the self-expanding element is slideable along the guidewire. In this configuration, the bump can limit the slidability of the self-expanding element. This can be because when the self-expanding element has expanded to the expanded diameter, a length of the self-expanding element decreases, and the bump limits the decrease in length and thus the expanded diameter.

Other examples have the combination of a steerable catheter and guidewire system that have a catheter having a catheter inner diameter forming a guidewire lumen and a catheter outer diameter. A guidewire can have a proximal end, a distal end, and a guidewire diameter. A self-expanding element can be disposed approximate to the distal end of the guidewire, and when the self-expanding element is disposed within the catheter, the self-expanding element has a contracted diameter. Here, the self-expanding element collapses in size and shape to enter the catheter to either be delivered to its target location in the body lumen or removed from the catheter so other tools can be disposed through the guidewire lumen. Alternately, when the self-expanding element is disposed outside the catheter, the self-expanding element has an expanded diameter, which is reached because it's expandable under its inherent properties.

In examples, the expanded diameter can be approximately 5% to 10% larger than the catheter outer diameter. As above, the expanded diameter is less than the body lumen diameter and the self-expanding element can be at least one of pear shaped, ovoid, and elliptical when at its expanded diameter. The self-expanding element can be inflatable or can include a plurality of deformable leafs and the contracted diameter permits the guidewire to be completely removed from the catheter.

Other examples are a method of advancing a steerable guidewire through a body lumen, using the steps of providing the steerable guidewire having a proximal end, a distal end, and a guidewire diameter. The self-expanding element can be disposed proximate the distal end and has a contracted and an expanded diameter. The self-expanding element can be expanded to the expanded diameter, which can be approximately 70% to 280% of the guidewire diameter.

Examples of the expanding step can further include a step of providing the expanded diameter less than a diameter of a body lumen. Further steps can be providing a catheter having a catheter diameter forming a guidewire lumen and advancing the steerable guidewire through the guidewire lumen. The self-expanding element can be disposed in the catheter with the contracted diameter and then the expanding step can further include disposing the self-expanding element outside the guidewire lumen to reach the expanded diameter. Additionally, the self-expanding element can be retracted into the guidewire lumen, thus changing the expanded diameter to the contracted diameter.

These and other examples can overcome the challenges in the prior art.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 1B is a side cross-section view of a known microcatheter and guidewire;

FIG. 1C is a side cross-section view of a known microcatheter and guidewire caught on a stent strut;

FIG. 3 is a front view of an example of a step feature for the guidewire of the present invention;

FIG. 4 is a cross-section view along line A-A of FIG. 2;
FIG. 5 is a cross-section view along line B-B of FIG. 2;
FIG. 6 is a cross-section view along line C-C of FIG. 2;
FIGS. 7A-7D are side cross-section views of an example of a steerable guidewire being deployed and retracted;

DETAILED DESCRIPTION

Figure 1A:
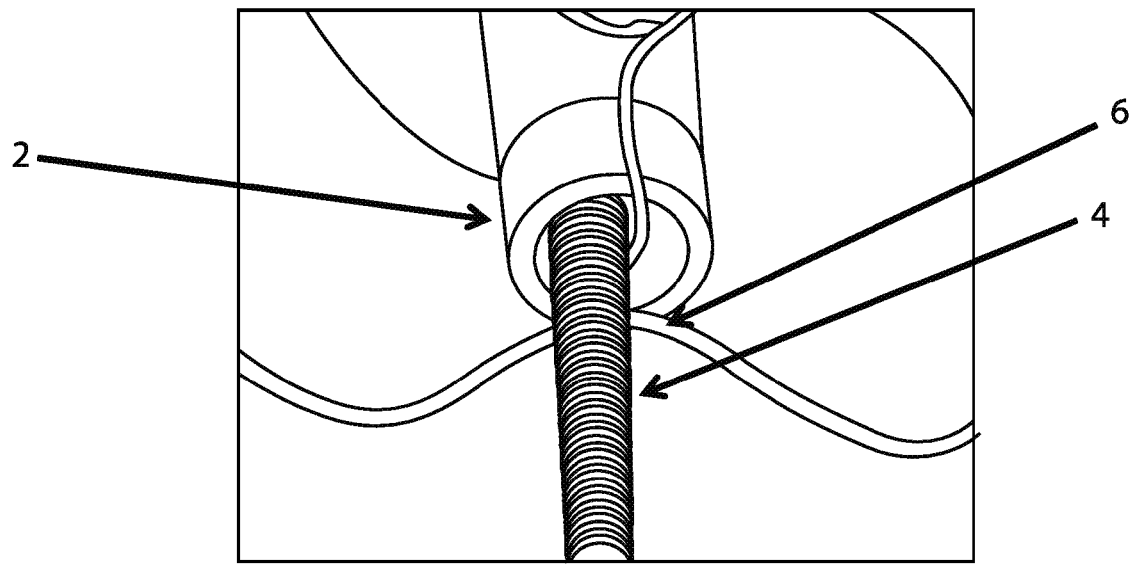
FIG. 1A is a top perspective view of a known microcatheter and guidewire caught on a stent strut.
Figure 2:
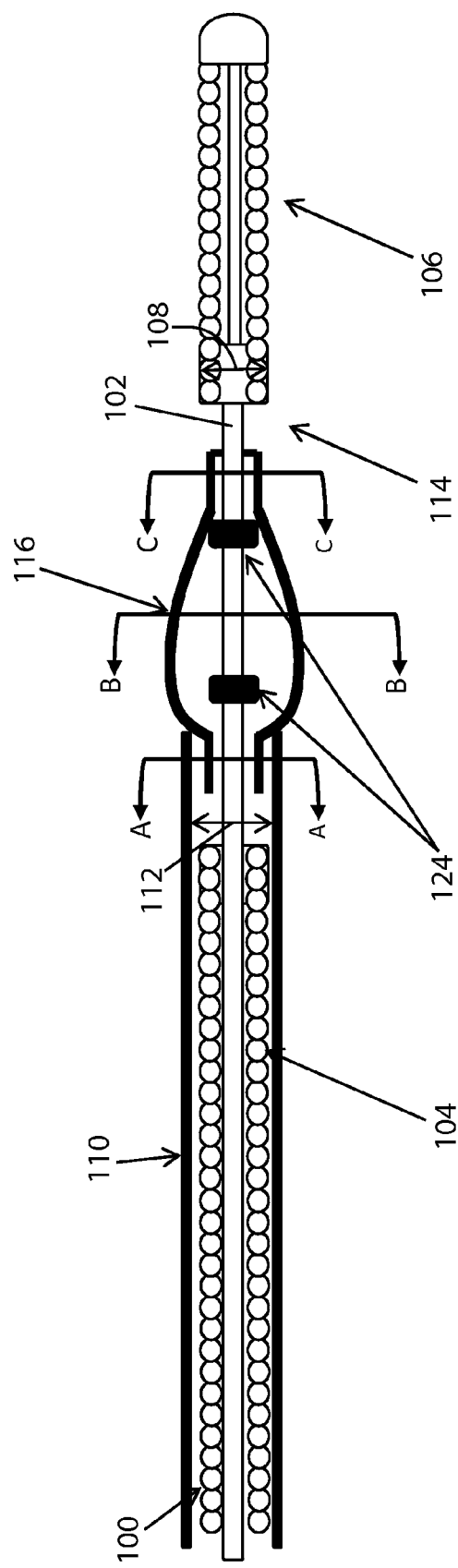
FIG. 2 is a side cross-section view of an example of a step feature for a guidewire of the present invention.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

FIGS. 2-6 illustrate an example of a step feature for a guidewire 100 of the present invention. The guidewire 100 can have a core 102, which extends the length of the guidewire 100, and a proximal end 104 and a distal end 106. The guidewire 100 and core 102 can be made of any material known to those of skill in the art for guidewires. The guidewire 100 has a guidewire diameter 108 so it can be directed through any size body lumen or passageway for a mammal. In one example, the guidewire 100 can be sized for neurovascular procedures. In another example, the guidewire diameter 108 is typically uniform across the length of the guidewire 100.

Disposed over the guidewire core 102 is a catheter/microcatheter 110. The catheter 110 has a catheter diameter 112 which is larger than the guidewire diameter 108, so that the guidewire 100 can pass through the inside 111 of the catheter 110. As above, the catheter 110 is sized so it can be directed through any size body lumen or passageway for a mammal, and in one example it can be sized for neurovascular procedures. The catheter 110 is made out of materials known to those of skill in the art, and in one example, can be relatively soft and pliable.

A gap 114 can be formed between the proximal 104 and distal 106 ends of the guidewire 100 over which can be disposed a self-expanding element 116. The self-expanding element 116 can be designed to expand and contract so as to increase and decrease its diameter. The self-expanding element 116 has a contracted diameter 118 which can be less than the catheter diameter 112 and, in one example, approximately equal to the guidewire diameter 108. The self-expanding element 116 typically has its contracted diameter 118 when disposed within the catheter 110. See, FIG. 7A. The self-expanding element 116 can also have an expanded diameter 120. The expanded diameter 120 can be greater than the guidewire diameter 108, and in one example, greater than the catheter diameter 112. The self-expanding element 116 can take its expanded diameter 120 once deployed from the catheter 110. See, FIG. 7B. The expanded diameter 120 is such that it can diminish or remove the ledge 8, as seen in the prior art. The leaves 122 can act as a "ramp" and this allows the guidewire 100 and catheter 110 to pass over the stent struts 6 of the stent cell 10, see FIG. 8.

The self-expanding element 116 can be radially expandable from the contracted diameter 118, in one example where the element 116 is not greater in diameter 118 than the diameter of the guidewire shaft 108, to the expanded diameter 120, in which the diameter 120 of the element 116 is greater than that of the guidewire 108. The self-expanding element 116 can be self-expanding under the influence of its inherent flexibility.

In one example, the self-expanding element 116 is a multi-leaf element. Each leaf 122 has the ability to flex so it can change shape and then return to its original shape. Thus the leaves 122 flex to allow the self-expanding element 116 to alternate between its contracted diameter 118 and expanded diameter 120. The self-expanding multi-leaf element 116 may be laser cut from a hypotube or fabricated from wires. The self-expanding element 116 may contain as few as three (3) or as many as twelve (12) leafs 122. In an example, some or all of the self-expanding multi-leaf element 116 can be radiopaque, allowing the surgeon to determine if the element 116 has been deployed from the catheter 110.

FIGS. 3-6 illustrate the self-expanding element 116 in its deployed state. FIG. 3 illustrates the leaves 122 creating the expanded diameter 120 greater than the catheter diameter 112. FIGS. 4-6 illustrate the self-expanding element 116 along the length of the gap 114 and how it can be, in an example, unfixed to the core 102. In a yet further example, the self-expanding element 116 can also be secured directly to the core 102 near the proximal end 104. In this configuration the self-expanding element 116 does not rotate or move axially over the core 102 (except for forward translation) but can be deployed into and out of the catheter 110.

In a further example, the self-expanding element 116 can rotate or move axially along the core 102 in the gap 114. The movement of the self-expanding element within the gap 114 can be controlled by a number of different features. In this example, an expansion/retraction bump 124 can be placed on the core 102 and under the leaves 122/self-expanding element 116. The expansion/retraction bumps 124 can have a larger outer diameter than an inner diameter of the leaves 122 on the self-expanding element 116. This can limit the amount of axial displacement of the self-expanding element 116. Additionally, one or both of the expansion/retraction bumps 124 may be radiopaque.

Figure 7A:
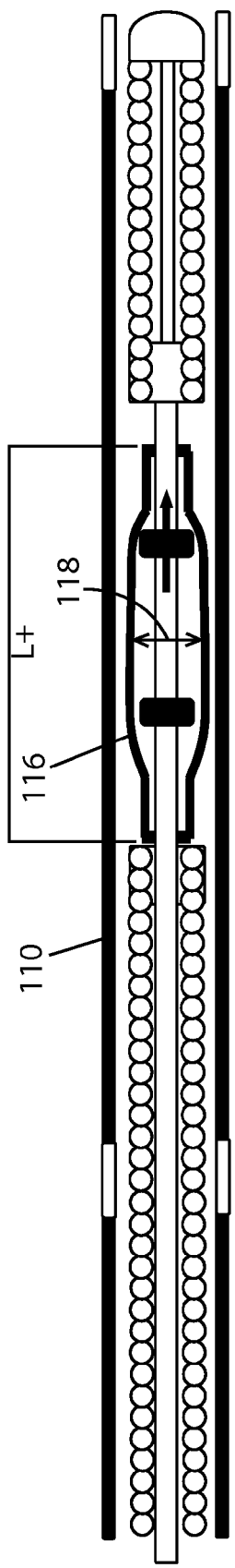
Figure 7B:
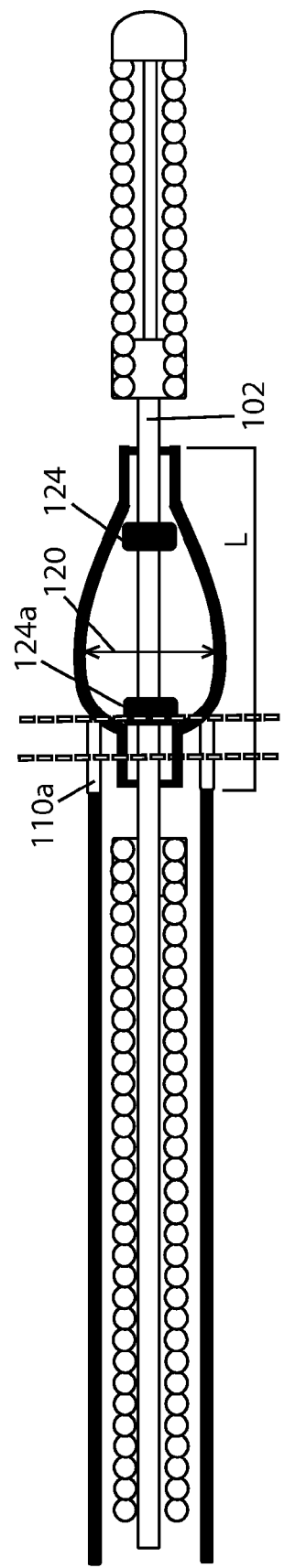
Figure 8:
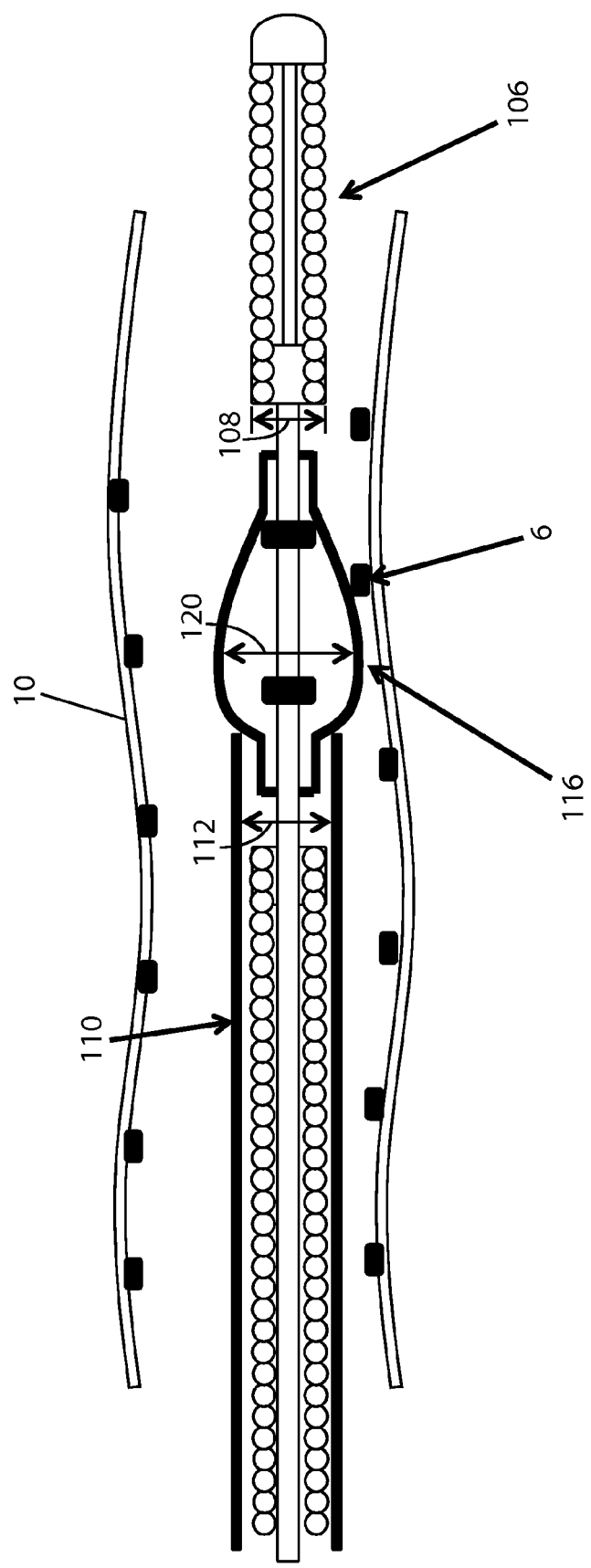
FIG. 8 is a side cross-section view of an example of a microcatheter and guidewire of the present invention avoiding being caught on a stent strut.

As illustrated in FIGS. 7A-7D, while tracking the guidewire 100 inside of a microcatheter 110, the self-expanding element 116 is constrained as shown on FIG. 7A. The self-expanding element 116 is located inside the microcatheter 110 by the mechanical interference between the larger distal expansion/retraction bump 124 and the distal self-expanding element leaf 122. The self-expanding element 116 opens once it is deployed out of the microcatheter 110, as shown in FIG. 7B. Alignment of a radiopaque proximal expansion/retraction bump 124a with a catheter distal marker 110a can indicate that the self-expanding element 116 is fully opened. Once deployed, the guidewire 100 and catheter 110 can be advanced in tandem over the stent cell 10 without the potential for the catheter's 110 tip getting caught on the stent struts 6. Compare FIG. 1C with FIG. 8. Note that the stent cell 10 could have been deployed during a previous procedure, and now the surgeon is performing a second procedure. FIGS. 7C and 7D illustrate the self-expanding element 116 collapsing back into the microcatheter 110 by pulling on the guidewire 100 until the self-expanding element 116 is driven inside of the microcatheter 110 by the mechanical interference between the expansion/retraction bump 124.

Another example of how the self-expanding element 116 functions is that, in its rest position, the leaves 122 flex to the expanded diameter 120. In this state, the overall length of the self-expanding element 116 is L. As the leaves 122 are "flattened", that is to say straightened to a more parallel position, the length of the self-expanding element 116 can be increased to L+. Thus, one or both of the ends of the self-expanding element 116 translate along the core 102. The self-expanding element 116 can be made from any spring or memory type metal or material. In one example, the material can be a nickel-titanium alloy (e.g. Nitinol). However, any element that can be expanded or contracted and deployed from a catheter can be used as the self-expanding element 116. Further, an example of the expanded diameter 120 is that it can be 5-10% greater than the catheter diameter 112. In examples, the expanded diameter 120 can be greater than the outer diameter of the catheter, but not significantly so as to prevent the catheter and guidewire from passing through the chosen body lumen.

In other examples, the expanded diameter 120 can be compared to the guidewire diameter 108. The expanded diameter 120 can range between approximately 70% to 280% of the guidewire diameter depending on the combinations of guidewires and catheters. Additionally, the shape of the self-expanding element 116 can be any shape that facilitates the passing of the catheter 110 over a stent strut 6. Examples of shapes are pear shaped, ovoid, and elliptical. Both the expanded diameter 120 and the shape of the self-expanding element 116 can be such that the leaves 122 are not designed to contact the walls of which ever body lumen the steerable wire 100 is passed through. In an example, the self-expanding element 116 does not assist in "centering" the guidewire/catheter system through the body lumen, on the contrary, the guidewire/catheter system needs some tolerance to the body lumen in order to move around the stent.

In use, the surgeon is typically aware that the patient has a previously deployed stent in the body lumen through which she needs to pass the guidewire and catheter. The surgeon can then choose to use the step feature for the steerable guidewire of the present invention. The self-expanding element 116 is typically deployed prior to reaching the stent, and its deployment verified using radio, X-ray or fluoroscopy imaging. Once the guidewire and catheter have passed the stent, and the catheter is in position for the new procedure, the surgeon can pull back on the guidewire, collapsing the self-expanding element, and fully remove the guidewire without complications from the element to proceed with the remainder of the surgical procedure.

Figure 9:
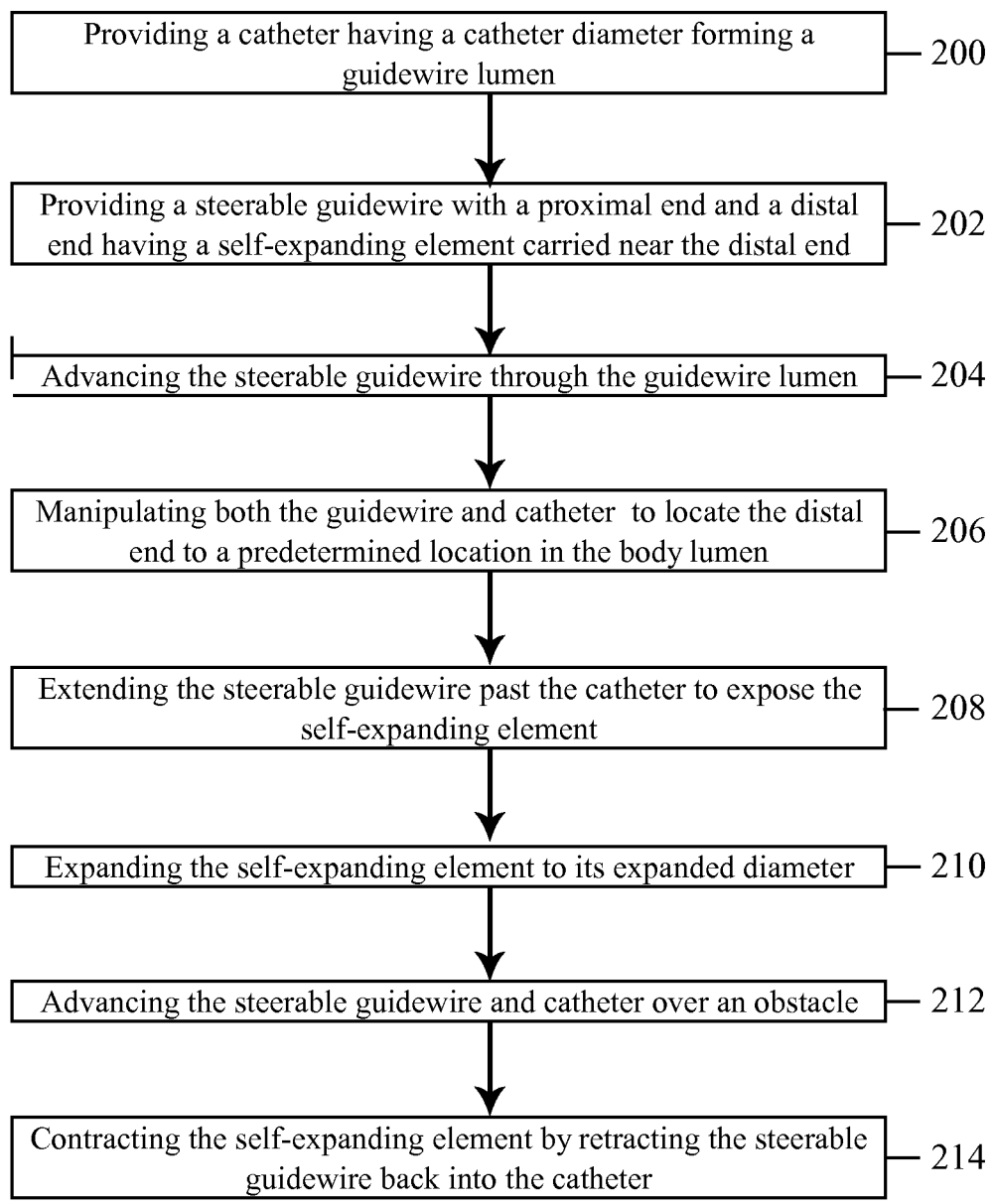
FIG. 9 is a flow chart of an example of a method of using a step feature for a guidewire.

FIG. 9 illustrates a method of advancing a steerable guidewire with a step function through a body lumen, which includes the step of providing a catheter 110 having a catheter diameter 112 that can form a guidewire lumen (step 200). A steerable guidewire 100 with a proximal end 104 and a distal end 106 having a self-expanding element 116 carried near the distal end 106 thereof can also be provided (step 202). The steerable guidewire 100 can be advanced through the guidewire lumen (step 204) and both the guidewire and catheter can be manipulated to locate the distal end 106 to a predetermined location in the body lumen (step 206). Either before or once an obstacle, such as a stent 6, is encountered, the steerable guidewire 100 is extended past the catheter 110 to expose the self-expanding element 116 (step 208). The self-expanding element 116 can be expanded to its expanded diameter 120 (step 210) and the steerable guidewire 100 and catheter can be advanced over the obstacle (step 212). The self-expanding element 116 can be contracted by retracting the steerable guidewire 100 back into the catheter 110 (step 214).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A step feature guidewire traversing previously disposed stent struts, comprising:
    a guidewire comprising a proximal end, a distal end, and a diameter;
    a self-expanding element disposed approximate to the distal end of the guidewire and having a contracted diameter and an expanded diameter, comprising a plurality of leaves that are non-intersecting with each other; and
    a bump disposed on the guidewire under the self-expanding element,
    wherein the self-expanding element is slideable along the guidewire,
    wherein the bump limits a slidability of the self-expanding element,
    wherein when the self-expanding element has the expanded diameter, a length of the self-expanding element decreases, and the bump limits the decrease in length and the expanded diameter,
    wherein the self-expanding element being expandable under inherent properties,
    wherein the expanded diameter is approximately 70% to 280% of the guidewire diameter, and
    wherein the self-expanding element forms a ramp with the non-intersecting leaves at the expanded diameter configured to pass over the previously disposed stent struts.

2. The step feature guidewire of claim 1, wherein the expanded diameter is less than a body lumen diameter.

3. The step feature guidewire of claim 1, wherein the self-expanding element is at least one of pear shaped, ovoid, and elliptical when at the expanded diameter.

4. A steerable catheter and guidewire system for passing over obstacles previously disposed in a body lumen, comprising:
    a catheter having a catheter inner diameter forming a guidewire lumen and a catheter outer diameter;
    a guidewire comprising a proximal end, a distal end, and a guidewire diameter; and
    a self-expanding element disposed approximate to the distal end of the guidewire, and comprising individual non-intersecting leaves,
    wherein when the self-expanding element is disposed within the catheter, the self-expanding element has a contracted diameter, wherein when the self-expanding element is completely disposed outside the catheter, the self-expanding element has an expanded diameter, wherein the self-expanding element being expandable under inherent properties, wherein the self-expanding element forms a ramp from the leaves within all or part of a space between the guidewire and the catheter outer diameter at the expanded diameter, and wherein the ramp is configured to be proximate the distal end of the catheter and to allow both the guidewire and the catheter to be advanced to pass over the previously disposed obstacles.

5. The steerable catheter and guidewire system of claim 4, wherein the expanded diameter is approximately 5% to 10% larger than the catheter outer diameter.

6. The steerable catheter and guidewire system of claim 4, wherein the expanded diameter is less than a body lumen diameter.

7. The steerable catheter and guidewire system of claim 4, wherein the self-expanding element is at least one of pear shaped, ovoid, and elliptical when at the expanded diameter.

8. The steerable catheter and guidewire system of claim 4, wherein the self-expanding element contracted diameter permits the guidewire to be completely removed from the catheter.

9. The steerable catheter and guidewire system of claim 4, further comprising a plurality of bumps disposed on the guidewire under the self-expanding element, wherein the self-expanding element comprises ends slideable along the guidewire;

wherein the plurality of bumps limit a slidability of the ends of the self-expanding element;

wherein when the self-expanding element has the expanded diameter, a length of the self-expanding element decreases, and the bumps limit the decrease in length and the expanded diameter.

10. A method of advancing a steerable guidewire through a body lumen having a previously disposed stent strut, comprising the steps of:

providing a steerable guidewire having a proximal end, a distal end, and a guidewire diameter;

providing a self-expanding element disposed proximate the distal end, having a contracted and an expanded diameter; and expanding the self-expanding element to the expanded diameter;

wherein the expanded diameter is approximately 70% to 280% of the guidewire diameter;

providing a catheter comprising a catheter inner diameter forming a guidewire lumen and an outer diameter;

advancing the steerable guidewire through the guidewire lumen;

disposing the self-expanding element in the catheter with the contracted diameter;

wherein the expanding step further comprises the step of:
  disposing the self-expanding element completely outside the guidewire lumen with the expanded diameter and forming a ramp with non-intersecting leaves of the self-expanding element within all or part of a space between the guidewire and the catheter outer diameter and, using the ramp to prevent all or part of the space from catching the previously disposed stent strut disposed in the body lumen.

11. The method of claim 10, wherein the expanding step further comprising the step of providing the expanded diameter less than a diameter of a body lumen.

12. The method of claim 10, further comprising the step of retracting the self-expanding element into the guidewire lumen changing the expanded diameter to the contracted diameter.

* * * * *